United States Patent
Liu et al.

(10) Patent No.: US 9,663,382 B2
(45) Date of Patent: May 30, 2017

(54) METHOD OF SYNTHESIZING ANATASE TIO₂ NANOSHEETS

(71) Applicant: NANYANG TECHNOLOGICAL UNIVERSITY, Singapore (SG)

(72) Inventors: Jiehua Liu, Singapore (SG); Xue-Wei Liu, Singapore (SG); Xiangfeng Wei, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 860 days.

(21) Appl. No.: 13/627,259

(22) Filed: Sep. 26, 2012

(65) Prior Publication Data

US 2013/0079520 A1 Mar. 28, 2013

Related U.S. Application Data

(60) Provisional application No. 61/539,222, filed on Sep. 26, 2011.

(51) Int. Cl.
*C01G 23/053* (2006.01)
*C07F 15/00* (2006.01)
*C07F 7/00* (2006.01)
*H01G 9/20* (2006.01)

(52) U.S. Cl.
CPC ............ *C01G 23/053* (2013.01); *C07F 7/006* (2013.01); *C07F 15/0046* (2013.01); *H01G 9/2031* (2013.01); *C01P 2002/72* (2013.01); *C01P 2004/03* (2013.01); *C01P 2004/04* (2013.01); *C01P 2004/24* (2013.01); *C01P 2006/12* (2013.01); *C01P 2006/14* (2013.01); *C01P 2006/17* (2013.01); *Y02E 10/542* (2013.01)

(58) Field of Classification Search
CPC .................................................... C01G 23/053
USPC .......................................... 423/610; 502/350
See application file for complete search history.

(56) References Cited

U.S. PATENT DOCUMENTS

| | | | |
|---|---|---|---|
| 6,350,946 B1 * | 2/2002 | Miyake et al. | 136/252 |
| 2002/0108649 A1 * | 8/2002 | Fujimori et al. | 136/263 |
| 2007/0264492 A1 * | 11/2007 | Mizuno et al. | 428/328 |

OTHER PUBLICATIONS

Wei et al., "Fabrication of O (dye)-terminated anatase TiO2 nanosheets for dye sensitized solar cells," Energy & Environmental Science 2011(4), pp. 2054-2057, Apr. 2011.*
Wen et al., "Single Nanocrystals of Anatase—Type TiO2 Prepared from Layered Titanate Nanosheets: Formation Mechanism and Characterization of Surface Properties," Langmuir 23(23), pp. 11782-11790, Oct. 2007.*
Liu et al., "Sandwich-Like, Stacked Ultrathin Titanate Nanosheets for Ultrafast Lithium Storage," Advanced Materials 23(8), pp. 998-1002, Dec. 2010.*

* cited by examiner

*Primary Examiner* — Melvin C Mayes
*Assistant Examiner* — James Corno
(74) *Attorney, Agent, or Firm* — Sughrue Mion, PLLC

(57) ABSTRACT

A method of synthesizing anatase TiO₂ nanosheets, the method comprising the steps of: (a) mixing a titanium complex with an ethanolamine derivative; (b) adding water to form a mixture; and (c) heating the mixture at a temperature ranging from about 150° C. to about 200° C. to obtain anatase TiO₂ nanosheets having O-terminated {100} facets.

7 Claims, 7 Drawing Sheets
(5 of 7 Drawing Sheet(s) Filed in Color)

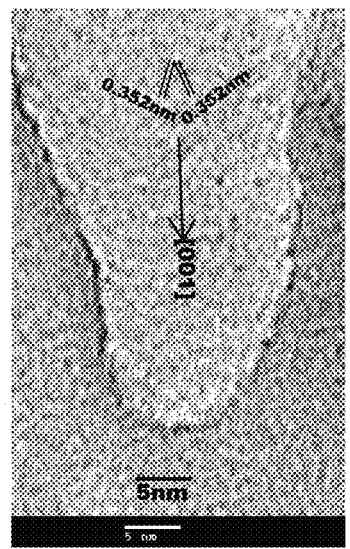 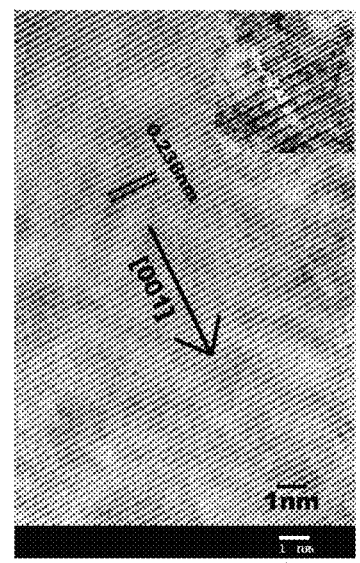
FIG. 3a          FIG. 3b
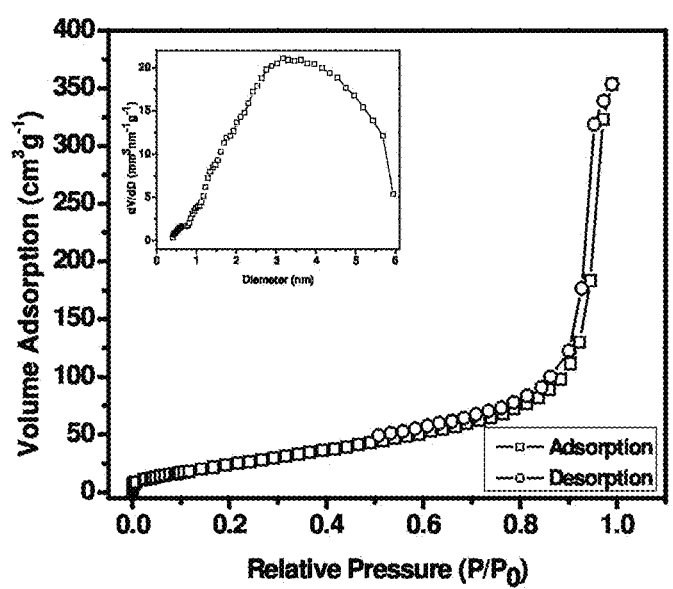
FIG. 4a

METHOD OF SYNTHESIZING ANATASE TiO₂ NANOSHEETS

TECHNICAL FIELD

This invention relates to a method of synthesizing anatase $TiO_2$ nanosheets, and in particular, but not exclusively, to a method of synthesizing anatase $TiO_2$ nanosheets for a dye-sensitized solar cell (DSSC).

BACKGROUND

Much progress has been made in studies on optimizing the performance of dye sensitized solar cells (DSSCs) in the last two decades.[1-6] $TiO_2$ films of photoanodes, serving as the electron acceptor and transport layer, play a key role in DSSCs.[7-11] Some key factors, such as the morphology, size, surface state, and crystalline structure, affect the electron transport and the amount of adsorbed dye on the $TiO_2$ photoanode.[11-15] In order to enhance light to electricity conversion efficiency (q), much effort has made to focus on the nano-architecture of $TiO_2$ with good crystallinity and high surface area.[16-19]

Recently, vertically oriented one-dimensional (1D) $TiO_2$ nanostructures, such as nanowires,[20] nanorods,[21-23] nanotubes,[24-27] and nanofibers,[28] have also been reported to remarkably enhance electron transport by creating a direct conduction pathway. However, their application is limited by the difficulties of large-area fabrication and high cost. Furthermore, two-dimensional $TiO_2$ frameworks, although drawing great attention, have not been successfully applied in DSSCs due to their thermal instability.[29]

Very recently, tetragonal faceted anatase nanorods with exposed {100} facets were successfully prepared from Na-titanate, which were obtained in NaOH solution, but the materials are not suitable for DSSCs due to their low surface area, submicro-size and Na-doping.[31]

SUMMARY

A low cost, high yield, one-pot method is devised to prepare single crystalline anatase $TiO_2$ nanosheets with exposed {100} facets, which remains stable even after calcination at 500° C. Film devices with anatase $TiO_2$ nanosheets have O-(dye)-terminated {100} facets having the lowest surface energy amidst all facets, and exhibit excellent η (7.03%) under simulated AM 1.5 sunlight irradiation. The result is much better than that of standard P-25 photoanodes (5.12%) under coincident conditions, by 1.37 times. It is believed that the anatase 100} facets bond with carboxyl groups of dyes more firmly than other facets.

According to a first aspect, there is provided a method of synthesizing anatase $TiO_2$ nanosheets, the method comprising the steps of: (a) mixing a titanium complex with an ethanolamine derivative; (b) adding water to form a mixture; and (c) heating the mixture at a temperature ranging from about 150° C. to about 200° C. to obtain anatase $TiO_2$ nanosheets having O-terminated {100} facets.

The method may further comprise (d) heating the anatase $TiO_2$ nanosheets having O-terminated {100} facets at a temperature ranging from about 400° C. to about 600° C. to obtain anatase $TiO_2$ nanosheets having activated {100} facets.

The method may further comprise, after step (c) and before step (d), washing with ethanol, centrifuging and drying the anatase $TiO_2$ nanosheets having O-terminated {100} facets at a temperature ranging from room temperature to about 200° C.

According to a second aspect, there is provided anatase $TiO_2$ nanosheets comprising exposed {100} facets.

The anatase $TiO_2$ nanosheets may be synthesized according to the method of the first aspect.

According to a third aspect, there is provided a method of fabricating a dye-sensitized solar cell, the method comprising: (a) mixing a titanium complex with an ethanolamine derivative; (b) adding water to form a mixture; (c) heating the mixture at a temperature ranging from about 150° C. to about 200° C. to obtain anatase $TiO_2$ nanosheets having O-terminated {100} facets; (d) heating the anatase $TiO_2$ nanosheets having O-terminated {100} facets at a temperature ranging from about 400° C. to about 600° C. to obtain anatase $TiO_2$ nanosheets having activated {100} facets; and (e) soaking the anatase $TiO_2$ nanosheets having activated {100} facets in a high performance dye solution to obtain anatase $TiO_2$ nanosheets having O-(dye)-terminated {100} facets.

The method may further comprise, immediately after step (c) and before step (d), washing with ethanol, centrifuging and drying the anatase $TiO_2$ nanosheets having O-terminated {100} facets at a temperature ranging from room temperature to about 200° C.

For all aspects, the titanium complex may be a titanium (IV) complex. According to a third aspect, there is provided a dye-sensitized solar cell comprising: anatase $TiO_2$ nanosheets having O-(dye)-terminated {100} facets.

The dye-sensitized solar cell may be fabricated according to the method of the second aspect.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In order that the invention may be fully understood and readily put into practical effect there shall now be described by way of non-limitative example only exemplary embodiments, the description being with reference to the accompanying illustrative drawings.

In the drawings:

FIG. 1 is a graph showing XRD patterns of an as-synthesized sample of anatase $TiO_2$ and TO-500, a synthesized sample of anatase $TiO_2$ annealed at 500° C. for 0.5 hours;

FIG. 2a is an FESEM image of a TO-500 sample FIG. 2b is a TEM image (b) of a TO-500 sample.

FIG. 3a is an HRTEM image showing $TiO_2$ nanosheets with lattice spaces of 0.352 nm corresponding to the (101) planes;

FIG. 3b is an HRTEM image showing $TiO_2$ nanosheets with lattice spaces of 0.238 nm corresponding to the (004) planes;

FIG. 4a is a graph of $N_2$ adsorption/desorption and pore size distribution (inset) of the as-synthesized $TiO_2$ nanosheets;

FIG. 4b is a graph of $N_2$ adsorption/desorption and pore size distribution (inset) of a TO-500 sample;

FIG. 5a is a graph of current-voltage characteristics of a dye-sensitized solar cell with a $TiO_2$ nanosheets film prepared according to the present method as a photoanode using N719 as a sensitizing dye;

FIG. 5b is a graph of current-voltage characteristics of a dye-sensitized solar cell with a P-25 (commercially available TiO$_2$) film as a photoanode using N719 as a sensitizing dye;

FIG. 6 is a current-voltage curve of a dye-sensitized solar cell with a anatase TiO$_2$ nanoparticles (average size<25) film;

FIG. 7a is a photograph of TO-500 and P-25 films;

FIG. 7b is a graph of an IPCE of device A and B with a TO-500 film and a P-25 film respectively, which were fabricated and tested using similar experimental procedures.

Figure 8A:
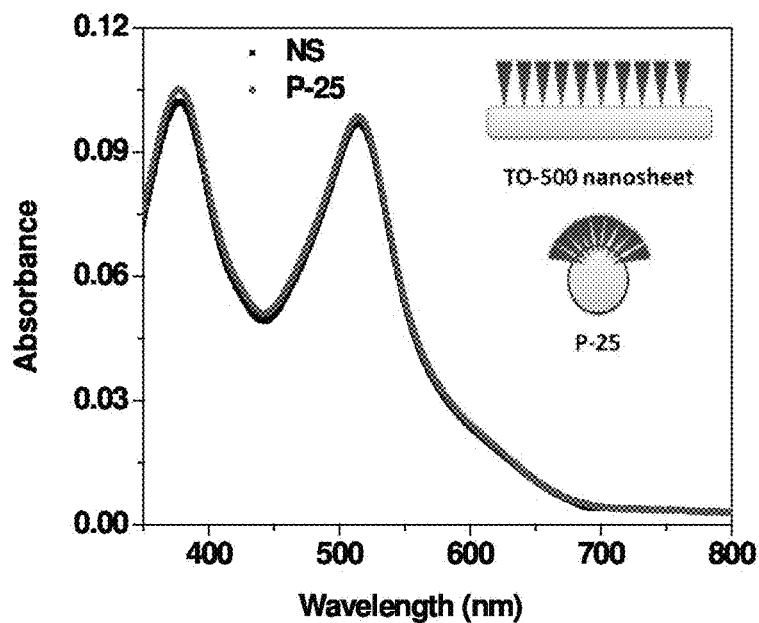
Figure 8B:
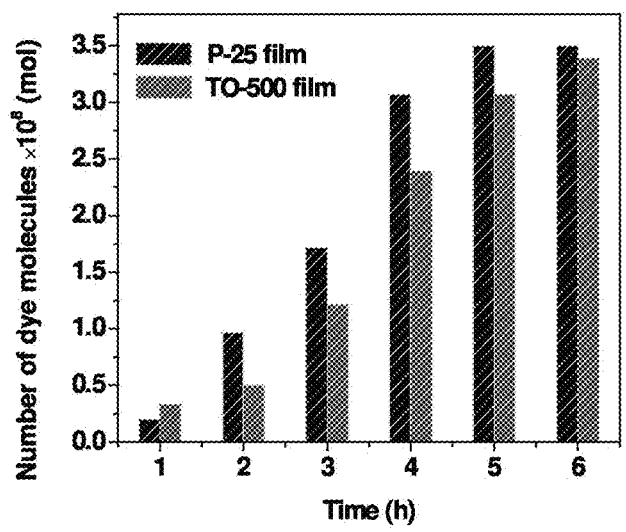
Figure 9:
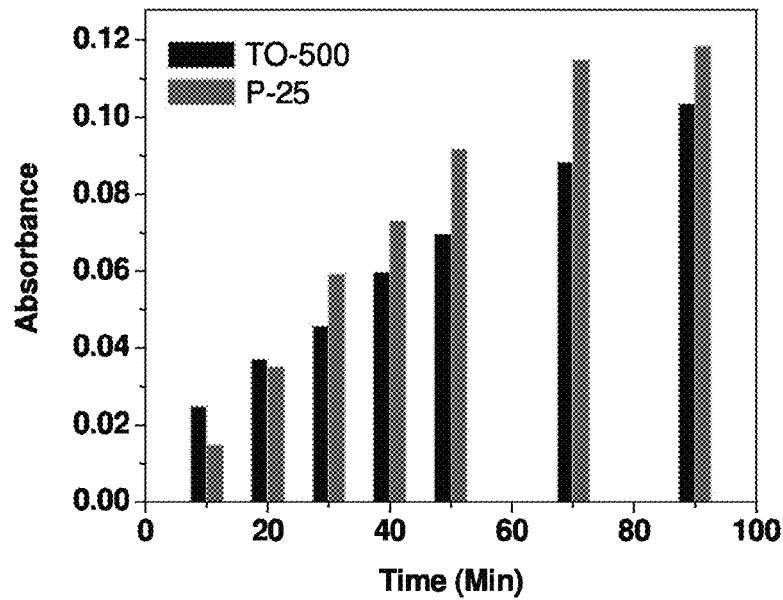
Figure 10:
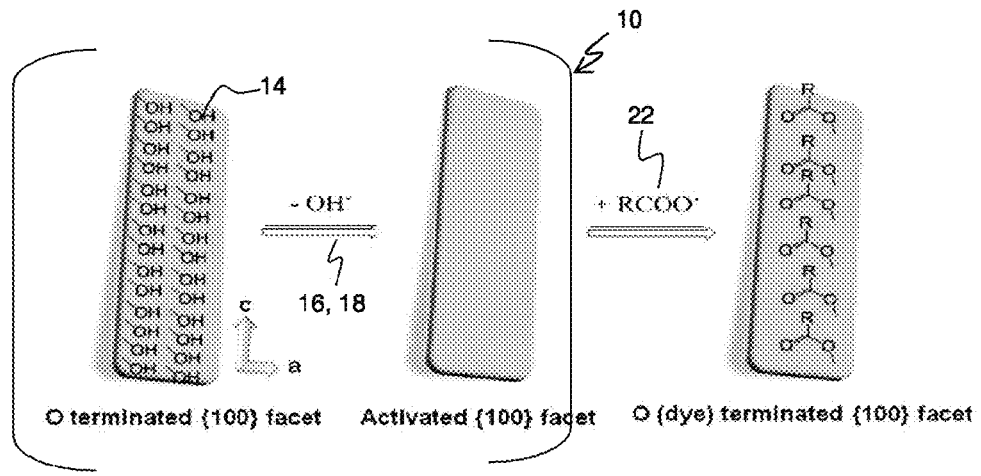
Figure 11:
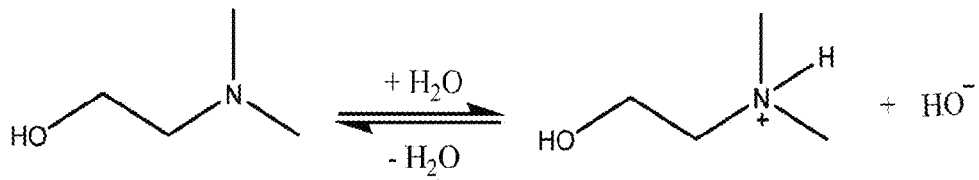

FIG. 8a is a UV-Vis spectra of desorbed dye from P-25 and TO-500 and the inset is the schemes of dye adsorbed by a TO-500 nanosheet and by a P-25 nanoparticle;

FIG. 8b is a chart of the amount of dye-desorption by a TO-500 film and a P-25 film at different times;

FIG. 9 is a chart of the absorbance of dye desorbed from TO-500 and P-25 powders at different times;

FIG. 10 is a schematic flow chart of a method of synthesis of 0 (dye) terminated TiO$_2$ nanosheets; and FIG. 11 is an equation of the reaction of DMEA with water.

DETAILED DESCRIPTION OF EXEMPLARY EMBODIMENTS

An exemplary method (10) of synthesizing anatase TiO$_2$ nanosheets will be described with reference to FIGS. 1 to 11 below.

Synthesis of Anatase TiO$_2$ Nanosheets

In the present method (10) as shown in FIG. 10, DMEA (N,N-dimethylethanolamine) and water are employed to synthesize anatase TiO$_2$ nanosheets. In an exemplary embodiment of the method (10), single crystalline anatase TiO$_2$ nanosheets were synthesized in a hydrothermal method (10) as follows: 19 g of titanium (IV) butoxide was dispersed in or mixed with 25 g of N,N-dimethylethanolamine (DMEA) under ultrasonic agitation. A suspension or mixture was formed by adding 16 g of distilled water rapidly (14), the mixture comprising Ti(OH)$_4$. The suspension or mixture was then transferred into a Teflon autoclave and heated at 150° C. for 16 hours (16), followed by filtering through nylon membrane filters with a pore size of 220 nm to obtain anatase TiO$_2$ nanosheets having O-terminated {100} facets. The filtered powder was washed with ethanol and centrifuged for three times and then dried at 70° C. (18). To obtain TO-500, the as-synthesized anatase TiO$_2$ nanosheets were further calcinated or heated at 500° C. for 0.5 h (18) to obtain anatase TiO$_2$ nanosheets having activated {100} facets.

The method (10) has unique advantages, in that: i) it offers OH$^-$ groups which are required to form O-terminated facets as shown in FIG. 11, the OH$^-$ groups being produced as a result of adding water to the mixture of DMEA and titanium (IV) butoxide where the water acts as a reactant for hydrolysis of the titanium (IV) butoxide; and ii) the boiling point of the method (10) is very close to its reaction temperature, which makes it a safe synthesis protocol, superior to use of solvents with lower boiling points. The resulting facets in the mixture can be easily activated by heat (18) and no doped ions exist in the stable TiO$_2$ bulk after annealing at 500° C. (18).

More importantly, dye adsorption on anatase {100} facets (22) is in fact an O-terminated process. The bond of conjugation in the formation of dye and the facets is very stable owing to the lowest surface energy. In this case, the unique {100} facets may minimize the chances of electron trapping from surface defects and hence improve the efficiency of light to electricity conversion. Therefore, the nanosheet-like anatase TiO$_2$ with exposed {100} facets synthesized according to the present method (10) is a desired material of the photoanode film for DSSCs.

Fabrication and Use of TiO$_2$ Thin-Film Photoanode for Dye-Sensitized Solar Cells (DSSCs)

The stable anatase TiO$_2$ nanosheets with exposed {100} facets synthesized according to the present method (10) are suitable for DSSCs owing to their high crystallinity and large surface area. The {100} facets were determined using high resolution TEM analysis, as will be described below. The existence of {100} facets (or not) depends on the crystal growth of anatase.

To investigate the photovoltaic properties of the anatase TiO$_2$ nanosheets synthesized according to the present method (10), a device A was constructed by applying platinum coated ITO glass as a counter electrode and a film composed of anatase TiO$_2$ nanosheets as a photoanode. The photoanode comprising a TiO$_2$ thin film prepared according to the present method (10) to be used in DSSCs was obtained after calcination or heating at 500° C. for 0.5 hours (18) in a muffle furnace under air atmosphere.

Compared to a typical photoanode of DSSCs, a usually provided scattering layer composed of nanosphere particles of 400 nm in size was not coated on top of the present crystalline TiO$_2$ layer of the TO-500 or the P-25, in order to focus on the effect of anatase TiO$_2$ nanosheets. Thus, the photoanodes coated with TiO$_2$ nanosheets film were deprived of the scattering layer.

Cells of the DSSC were assembled with the prepared photoanodes after soaking in 0.3 mM N719 solution in acetonitrile/tert-butyl alcohol (1:1) solvent mixture overnight (22). According to its supplier Dyesol Corporation, N719 is Dyesol's B2 dye, a modification of the B4 dye, to increase cell voltage. It is the most common high performance dye and has the following structure:

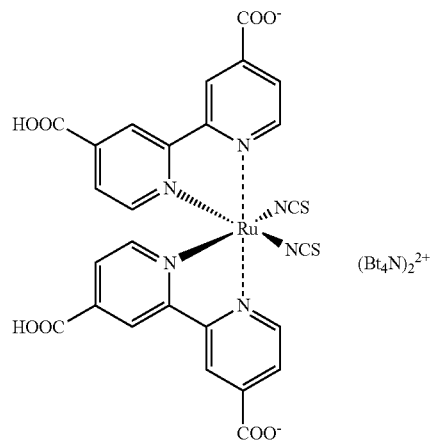

Platinum counter electrodes were made by sputtering on the transparent ITO glass. The electrolyte (EL-HPE) employed was also purchased from Dyesol Corporation.

The transparent ITO glass employed as the photoanode substrate was treated with TiCl$_4$ before TiO$_2$ paste casting.

In order to gauge the performance of device A, a device B with a photoanode composed of standard P-25 TiO$_2$ was fabricated and tested using similar procedures. To do so, a paste of commercially available $TiO_2$ (P-25) was prepared using a commercially known method[1]. The obtained $TiO_2$ paste was coated on transparent ITO glass via a known doctor-blade method. It should be noted that the transparent ITO glass was treated with 40 mM $TiCl_4$ solution for several seconds at room temperature before coating with the $TiO_2$ paste.

In order to focus on the effect of single crystalline anatase nanosheets, the photoanodes prepared and compared were coated with only a single layer of TO-500 nanosheet. The TO-500 film and P-25 film have a same thickness of 13.7 µm.

Characterization and Analysis

XRD Analysis

Figure 1:
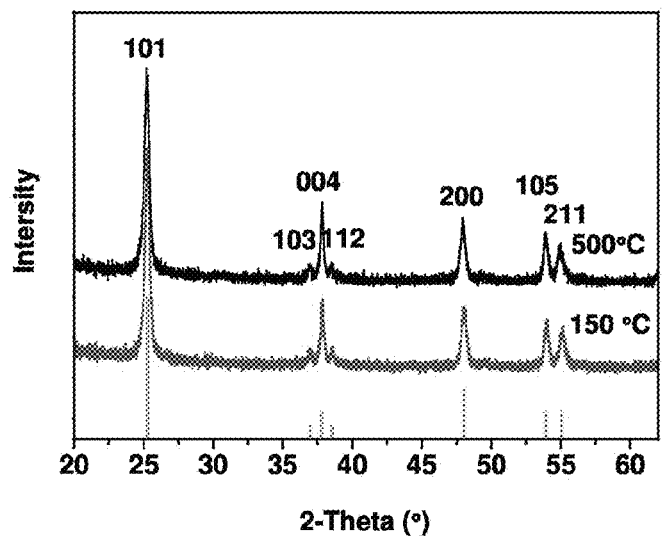

The crystalline structure and stability of anatase $TiO_2$ nanosheets synthesized according to the present method were examined by powder X-ray diffraction as shown in FIG. 1.

The XRD patterns were obtained with a D8 diffractometer with Cu—KR radiation at a wavelength of λ=1.54056 Å.

As can be seen, the pattern of an as-synthesized sample coincides with that of TO-500, indicating that the stable anatase phase was formed by a hydrothermal process. It is noteworthy that the intensity of (004) is higher than that of the standard anatase $TiO_2$ phase (JCPDS: 21-1272), which suggests dominant crystal growth along the [001] direction.

Electron Microscopy Analysis

The morphology of an as-synthesized sample and TO-500 was analyzed by field emission scanning electron microscopy (FESEM) and transmission electron microscopy (TEM). TEM images were obtained using TEM models nos. JEOL JEM-1400 and JEOL 2(10)F. FESEM images were recorded with an SEM model no. JEOL JSM 6700F.

Figure 2A:
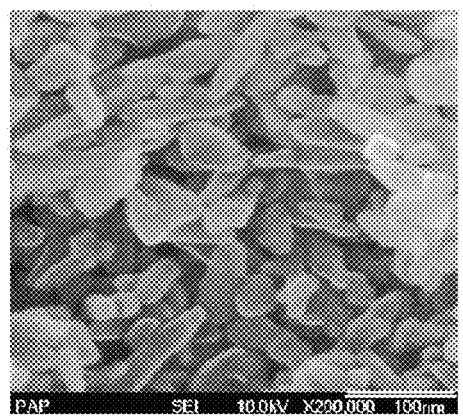
Figure 2B:
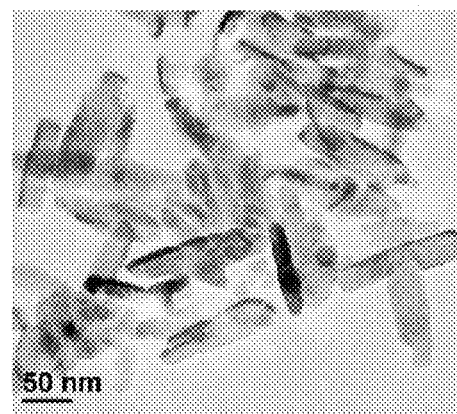

$TiO_2$ nanosheets with a length of 90-120 nm, a width of 20-40 nm and a thickness of ~5 nm can be seen from the FESEM image (FIG. 2a) of TO-500 samples. A TEM image of TO-500 shown in FIG. 2b is in conformity with the FESEM image, which also shows a sheet-like framework even after heat treatment at 500° C.

To determine the crystal facets of the anatase $TiO_2$ nanosheets synthesized according to the present method, high-resolution TEM (HRTEM) was employed. As shown in the images provided in FIGS. 3a and 3b, lattice spaces of the $TiO_2$ nanosheets of 0.35 nm and 0.24 nm respectively corresponding to the (101) and (004) planes of the anatase phase were determined when lying flat as shown in FIGS. 3a and 3b, which is consistent with the above XRD and TEM analysis. Crystal growth of $TiO_2$ nanosheets along the [001] direction was observed as shown in FIG. 3b, indicating that the stable anatase $TiO_2$ nanosheets could be formed[32] using the present method (10), having exposed {100} facets.

Nitrogen Adsorption-Desorption Analysis

Figure 4B:
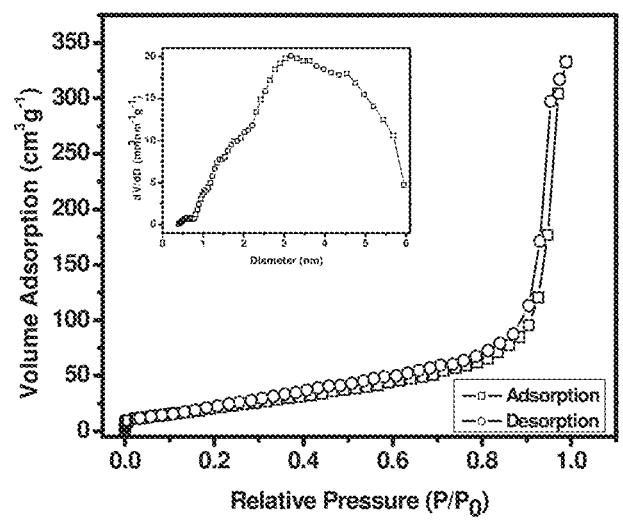

Nitrogen adsorption-desorption curves and pore distribution of an as-synthesized $TiO_2$ sample and TO-500 were further investigated as shown in FIGS. 4a and 4b. $N_2$ adsorption-desorption isotherms were conducted at 77K on a Micromeritics Tristar 3000 analyzer. BET surface areas and pore-size distribution curves were concluded using adsorption data.

As can be seen, there are no significant differences in adsorption-desorption and pore-distribution curves of the $TiO_2$ samples prepared according to the present method (10) before and after calcination or heating. The surface area of an as-synthesized sample and TO-500 are 108 and 90 $m^2 g^{-1}$ respectively, calculated from the $N_2$ adsorption isotherm using the DFT (density functional theory) method. The surface area of TO-500 is much larger than the surface area (55 $m^2 g^{-1}$) of the standard P-25. This indicates that the $TiO_2$ nanosheets can provide a large surface area for adsorption of dye in dye sensitized solar cells.

Moreover, the small pore volume of TO-500 is 0.072 $cm^3 g^{-1}$, which is filled with an extremely small amount of electrolyte. Therefore, the small pore volume can effectively reduce the effect of colored electrolyte.

Current Density-Voltage Analysis

Figure 5A:
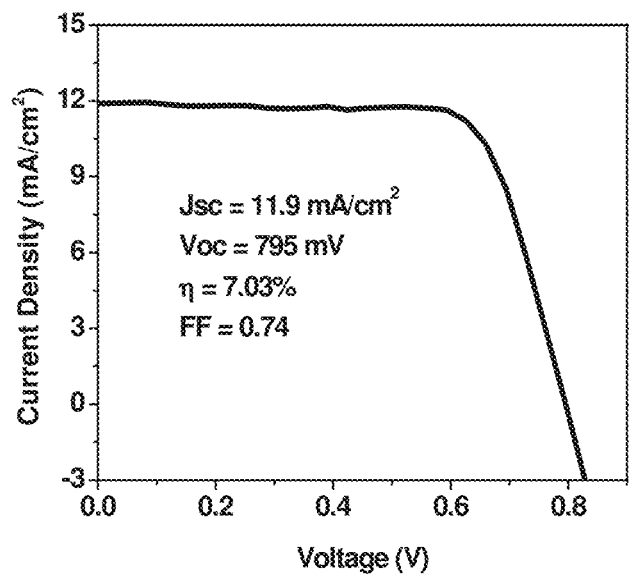

Current density-voltage curves were collected from device A by following a reported method.[33] As shown in FIG. 5a, the yield of light to electricity conversion efficiency of 7.03% was observed with a high fill factor of 0.74.

Figure 5B:
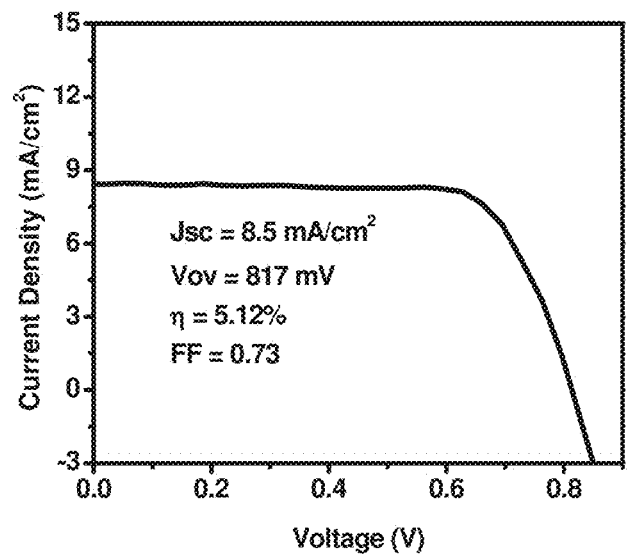

From current density-voltage characteristics of device B shown in FIG. 5b, it can be seen that its power conversion efficiency and fill factor are 5.12% and 0.73 respectively, much lower than the results of device A.

Figure 6:
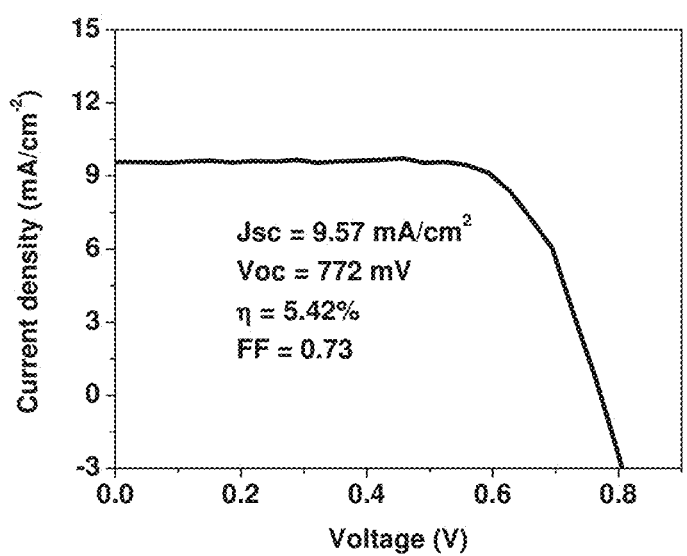

A current-voltage curve of the solar cell with anatase nanoparticles (its average size<25 nm) film is also provided in FIG. 6. Due to the large amount of adsorbed dye on the anatase film, its light to electricity conversion efficiency is 5.42%, which is only slightly more efficient than 5.12% of P-25 film.

Figure 7A:
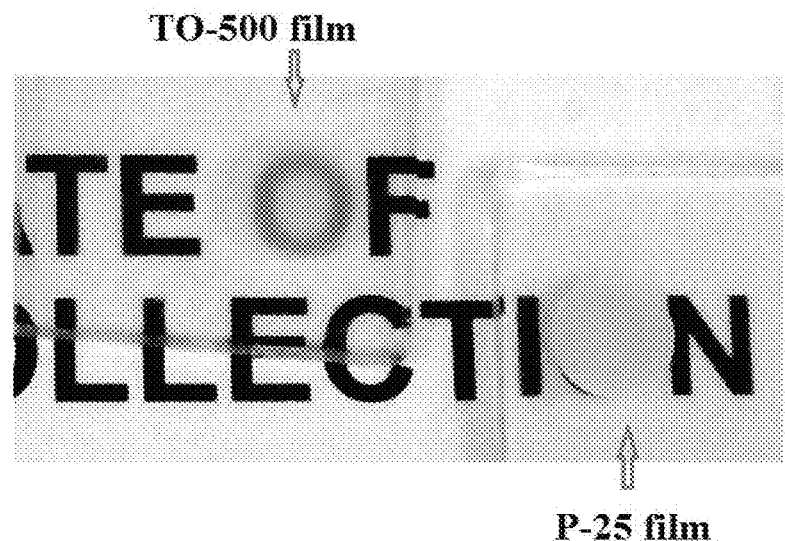
Figure 7B:
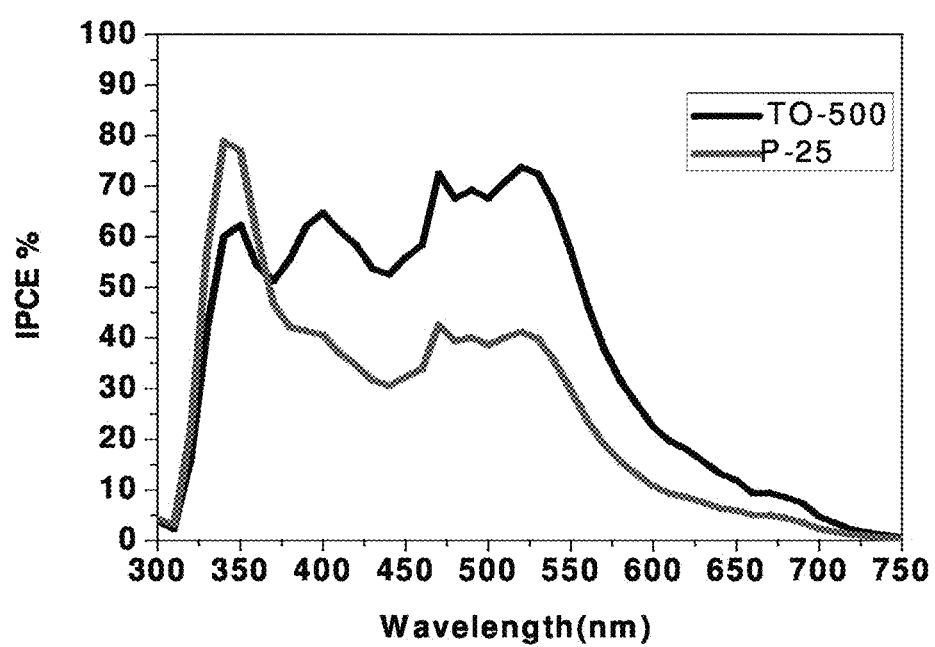

Incident photon to current efficiency (IPCE), which is directly affected by grain morphology and surface area, is commonly used to estimate the performance of $TiO_2$ photoanode films. As can be seen in the photograph of bare TO-500 and P-25 films in FIG. 7a, the TO-500 film has a better transmittance than P-25 film. A comparison of the IPCE of device A and B as depicted in FIG. 7b shows that the IPCE of device A with TO-500 film increases significantly from 375 nm to 750 nm.

The results show that the device with TO-500 film is suitable to improve the light to electricity conversion efficiency at visible light region. That is, the photoanode with TO-500 film can enhance the efficient electron transportation. Thus, $TiO_2$ nanosheets with exposed {100} facets may improve the efficiency of electron transport owing to the lowest surface energy on the O (dye) terminated facets.

Dye Adsorption and Desorption

The adsorbed amount of dye molecules and the number of dye-desorption at different times were determined to further confirm that the {100} facets of TO-500 nanosheets could bond with carboxyl groups of dyes more firmly than {101} facets of P-25. Dye-desorption experiments were processed in a 5 ml of 0.1M NaOH water/ethanol (1:1, v/v) mixed solution.

FIG. 8a shows the UV-Vis absorption spectra of N719 desorbed from TO-500 and P-25 films after desorption for 8 hours. UV-Vis absorption spectra were measured using a JASCO V-670 spectrophotometer.

The amount of dye molecules desorbed from the TO-500 film is close to the value obtained for the P-25 film. It suggests that almost the same amounts of dye were adsorbed on TO-500 and P-25 films. It is generally assumed that the larger surface area (90 $m^2 g^{-1}$) of the anatase nanosheets prepared according to the present method (10), when compared to 55 $m^2 g^{-1}$ of the standard P-25, may provide more sites for N719 molecules adsorption. However, in actual fact, the adsorbed amounts of dye on TO-500 and P-25 films were almost equal ($3.46\times10^{-8}$ and $3.52\times10^{-8}$ mol respectively). The main reason may be that P-25 has more grain boundaries than TO-500 nanosheet, on which N719 molecule with a big head could be assembled like micellar structure. The schemes of dye adsorbed TO-500 and P-25 are provided as the inset of FIG. 4a. The other possible reason is that some TO-500 nanosheets may overlap each other in the fabrication process of film electrode, which limits the amount of absorbed dyes.

FIG. 8b shows the amount of dye molecules desorbed from TO-500 and P-25 films at different times. Due to many interspaces at the dye layer and TO-500 interface, OH⁻ groups could easily diffuse into the single-molecule layer of dye on TO-500 interface. The amount of desorbed dye from the TO-500 film is more than that from the P-25 film at the first hour. Once the micelle-like layer was destroyed, the dye on the P-25 film is easier to be replaced with a hydroxyl group than that on TO-500. This result demonstrates that the {100} facets of TO-500 nanosheets could form more stable bonding with N719 molecule than the {101} facets of P-25.

To investigate the effect of diffusion paths, powders of TO-500 and P-25 were employed in the dye-desorption experiments. The results depicted in FIG. 9 show that the dye-desorption curves of the powders have similar properties as the dye-desorption curves of the films depicted in FIG. 8b. However, the dye-desorption rates for the powders are faster than that in the films owing to their short diffusion paths of desorbed dyes.

Although both electrodes produce comparable light harvesting owing to almost the same amounts of dye, the efficiency of device A with the TO-500 film is about 1.37 times higher than that of device B with the P-25 film. There are two main reasons for the increased photocurrent density. Firstly, the value of the diffusion coefficient of TO-500 may be higher than that for P-25 owing to the effect of grain boundaries, which minimize electron loss in the transfer process.[34] Secondly, the dye-terminated 2D structure of TO-500 with low surface energy may slow down the back transfer of electrons to $I_3^-$ and the oxidized dye.

On the other hand, the decreased number of contact grain boundaries also contributes to the highly efficient electron transport along highly crystallized nanosheets. In the TO-500 film, the stable bonding with N719 and unique structure for internal light scattering could enhance its IPCE and hence contribute to its higher light to electricity conversion efficiency when compared against the P-25 film.

In conclusion, single-crystal $TiO_2$ nanosheets in large scale with exposed {100} facets can be synthesized in a one-pot method (10) as described above. The facile and ideal (O-terminated-activated-O(dye)-terminated) processes make the material more compelling to DSSCs. The power conversion efficiency of the device with the $TiO_2$ nanosheets film synthesized according to the present method (10) could be up to 7.03%, superior to 5.12% of the device with P-25 film photoanode.

The present method (10) thus gives fresh impetus to the fabrication of $TiO_2$ electrode materials for DSSCs.

Whilst there has been described in the foregoing description exemplary embodiments of the present invention, it will be understood by those skilled in the technology concerned that many variations in details of design, construction and/or operation may be made without departing from the present invention. For example, while a temperature of 150° C. was used to heat (16) the suspension formed (14) in the exemplary embodiment, it will be understood that the heating temperature can range from about 150° C. to about 200° C. While a temperature of 500° C. was used to calcinate or heat (18) the as-synthesized anatase $TiO_2$ nanosheets to obtain the activated {100} facets, it will be understood that the this temperature can range from about 400° C. to about 600° C. While a temperature of 70° C. was used to dry the filtered powder, it will be understood that the drying temperature can range from room temperature to about 200° C. While titanium (IV) butoxide was described above as the source of titanium used, other titanium (IV) complexes such as titanium isopropoxide, titanium ethoxide and titanium tetrachloride may also be used, or alternatively, titanium (III) complexes may also be used. While N,N-dimethylethanolamine was described above as the solvent used, other ethanolamine derivative solvents can also be used.

REFERENCES

1. Odobel, F.; Le Pleux, L.; Pellegrin, Y.; Blart, E., New photovoltaic devices based on the sensitization of p-type semiconductors: challenges and opportunities. *Acc. Chem. Res.* 2010, 43, (8), 1063-1071.
2. Hagfeldt, A.; Boschloo, G.; Sun, L. C.; Kloo, L.; Pettersson, H., Dye-sensitized solar cells. *Chem. Rev.* 2010, 110, (11), 6595-6663.
3. Ning, Z. J.; Fu, Y.; Tian, H., Improvement of dye-sensitized solar cells: what we know and what we need to know. *Energy Environ. Sci.* 2010, 3, (9), 1170-1181.
4. Gratzel, M., Recent advances in sensitized mesoscopic solar cells. *Acc. Chem. Res.* 2009, 42, (11), 1788-1798.
5. Mishra, A.; Fischer, M. K. R.; Bauerle, P., Metal-free organic dyes for dye-sensitized solar cells: from structure: property relationships to design rules. *Angew. Chem. Int. Ed.* 2009, 48, (14), 2474-2499.
6. Hamann, T. W.; Jensen, R. A.; Martinson, A. B. F.; Van Ryswyk, H.; Hupp, J. T., Advancing beyond current generation dye-sensitized solar cells. *Energy Environ. Sci.* 2008, 1, (1), 66-78.
7. Oregan, B.; Gratzel, M., A low-cost, High-efficiency solar-cell based on dye-sensitized colloidal $TiO_2$ films. *Nature* 1991, 353, (6346), 737-740.
8. Nazeeruddin, M. K.; Kay, A.; Rodicio, I.; Humphrybaker, R.; Muller, E.; Liska, P.; Vlachopoulos, N.; Gratzel, M., Conversion of light to electricity by cis-$X_2$bis(2,2'-bipyridyl-4,4'-dicarboxylate)ruthenium(II) charge-transfer sensitizers (X=Cl⁻, Br⁻, I⁻, CN⁻, and SCN⁻) on nanocrystalline $TiO_2$ electrodes. *J. Am. Chem. Soc.* 1993, 115, (14), 6382-6390.
9. Bach, U.; Lupo, D.; Comte, P.; Moser, J. E.; Weissortel, F.; Salbeck, J.; Spreitzer, H.; Gratzel, M., Solid-state dye-sensitized mesoporous $TiO_2$ solar cells with high photon-to-electron conversion efficiencies. *Nature* 1998, 395, (6702), 583-585.
10. Law, M.; Greene, L. E.; Johnson, J. C.; Saykally, R.; Yang, P. D., Nanowire dye-sensitized solar cells. *Nat. Mater.* 2005, 4, (6), 455-459.
11. Park, N. G.; van de Lagemaat, J.; Frank, A. J., Comparison of dye-sensitized rutile- and anatase-based $TiO_2$ solar cells. *J. Phys. Chem. B* 2000, 104, (38), 8989-8994.
12. Wang, R.; Hashimoto, K.; Fujishima, A.; Chikuni, M.; Kojima, E.; Kitamura, A.; Shimohigoshi, M.; Watanabe, T., Photogeneration of highly amphiphilic $TiO_2$ surfaces. *Adv. Mater.* 1998, 10, (2), 135-138.
13. Huang, S. Y.; Schlichthorl, G.; Nozik, A. J.; Gratzel, M.; Frank, A. J., Charge recombination in dye-sensitized nanocrystalline $TiO_2$ solar cells. *J. Phys. Chem. B* 1997, 101, (14), 2576-2582.
14. Kim, D.; Lee, K.; Roy, P.; Birajdar, B. I.; Spiecker, E.; Schmuki, P., Formation of a non-thickness-limited titanium dioxide mesosponge and its use in dye-sensitized solar cells. *Angew. Chem. Int. Ed.* 2009, 48, (49), 9326-9329.
15. Qiu, Y. C.; Chen, W.; Yang, S. H., Double-layered photoanodes from variable-size anatase $TiO_2$ nano- 16. Wang, M.; Chen, P.; Humphry-Baker, R.; Zakeeruddin, S. M.; Gratzel, M., The influence of charge transport and recombination on the performance of dye-sensitized solar cells. *Chemphyschem* 2009, 10, (1), 290-299.
17. Liu, B.; Aydil, E. S., Growth of oriented single-crystalline rutile $TiO_2$ nanorods on transparent conducting substrates for dye-sensitized solar cells. *J. Am. Chem. Soc.* 2009, 131, (11), 3985-3990.
18. Jiu, J. T.; Isoda, S.; Wang, F. M.; Adachi, M., Dye-sensitized solar cells based on a single-crystalline $TiO_2$ nanorod film. *J. Phys. Chem. B* 2006, 110, (5), 2087-2092.
19. Kumar, A.; Madaria, A. R.; Zhou, C. W., Growth of aligned single-crystalline rutile $TiO_2$ nanowires on arbitrary substrates and their application in dye-sensitized solar cells. *J. Phys. Chem. C* 2010, 114, (17), 7787-7792.
20. Feng, X. J.; Shankar, K.; Varghese, 0. K.; Paulose, M.; Latempa, T. J.; Grimes, C. A., Vertically aligned single crystal $TiO_2$ nanowire arrays grown directly on transparent conducting oxide coated glass: synthesis details and applications. *Nano Lett.* 2008, 8, (11), 3781-3786.
21. Melcarne, G.; De Marco, L.; Carlino, E.; Martina, F.; Manca, M.; Cingolani, R.; Gigli, G.; Ciccarella, G., Surfactant-free synthesis of pure anatase $TiO_2$ nanorods suitable for dye-sensitized solar cells. *J. Mater. Chem.* 2010, 20, (34), 7248-7254.
22. Fujihara, K.; Kumar, A.; Jose, R.; Ramakrishna, S.; Uchida, S., Spray deposition of electrospun $TiO_2$ nanorods for dye-sensitized solar cell. *Nanotechnology* 2007, 18, (36), 365709.
23. De Marco, L.; Manca, M.; Giannuzzi, R.; Malara, F.; Melcarne, G.; Ciccarella, G.; Zama, I.; Cingolani, R.; Gigli, G., Novel preparation method of $TiO_2$-nanorod-based photoelectrodes for dye-sensitized solar cells with improved light-harvesting efficiency. *J. Phys. Chem. C* 2010, 114, (9), 4228-4236.
24. Xu, C. K.; Shin, P. H.; Cao, L. L.; Wu, J. M.; Gao, D., Ordered $TiO_2$ nanotube arrays on transparent conductive oxide for dye-sensitized solar cells. *Chem. Mater.* 2010, 22, (1), 143-148.
25. Wang, J.; Lin, Z. Q., Dye-sensitized $TiO_2$ nanotube solar cells with markedly enhanced performance via rational surface engineering. *Chem. Mater.* 2010, 22, (2), 579-584.
26. Li, L. L.; Tsai, C. Y.; Wu, H. P.; Chen, C. C.; Diau, E. W. G., Fabrication of long $TiO_2$ nanotube arrays in a short time using a hybrid anodic method for highly efficient dye-sensitized solar cells. *J. Mater. Chem.* 2010, 20, (14), 2753-2819.
27. Kang, T. S.; Smith, A. P.; Taylor, B. E.; Durstock, M. F., Fabrication of highly-ordered $TiO_2$ nanotube arrays and their use in dye-sensitized solar cells. *Nano Lett.* 2009, 9, (2), 601-606.
28. Ghadiri, E.; Taghavinia, N.; Zakeeruddin, S. M.; Gratzel, M.; Moser, J. E., Enhanced electron collection efficiency in dye-sensitized solar cells based on nanostructured $TiO_2$ hollow fibers. *Nano Lett.* 2010, 10, (5), 1632-1638.
29. Pavasupree, S.; Ngamsinlapasathian, S.; Suzuki, Y.; Yoshikawa, S., Synthesis and dye-sensitized solar cell performance of nanorods/nanoparticles $TiO_2$ from high surface area nanosheet $TiO_2$. *J. Nanosci. Nanotech.* 2006, 6, (12), 3685-3692.
30. Barnard, A. S.; Curtiss, L. A., Prediction of $TiO_2$ nanoparticle phase and shape transitions controlled by surface chemistry. *Nano Lett.* 2005, 5, (7), 1261-1266.
31. Li, J. M.; Xu, D. S., Tetragonal faceted-nanorods of anatase $TiO_2$ single crystals with a large percentage of active {100} facets. *Chem. Commun.* 2010, 46, (13), 2301-2303.
32. Adachi, M.; Murata, Y.; Takao, J.; Jiu, J. T.; Sakamoto, M.; Wang, F. M.,
Highly efficient dye-sensitized solar cells with a titania thin-film electrode composed of a network structure of single-crystal-like $TiO_2$ nanowires made by the "oriented attachment" mechanism. *J. Am. Chem. Soc.* 2004, 126, (45), 14943-14949.
33. Koide, N.; Han, L. Y., Measuring methods of cell performance of dye-sensitized solar cells. *Rev. Sci. Instrum.* 2004, 75, (9), 2828-2831.
34. Forro, L.; Chauvet, 0.; Emin, D.; Zuppiroli, L.; Berger, H.; Levy, F., HIGH-mobility n-type charge-carriers in large single-crystals of anatase ($TiO_2$). *J. Appl. Phys.* 1994, 75, (1), 633-635.

The invention claimed is:

1. A method of synthesizing anatase $TiO_2$ nanosheets, the method comprising the steps of:
 (a) mixing a titanium complex with an ethanolamine derivative;
 (b) adding sufficient water to completely hydrolyze the titanium complex to form a mixture, the mixture comprising $Ti(OH)_4$; and
 (c) heating the mixture at only one temperature ranging from about 150° C. to about 200° C. to obtain anatase $TiO_2$ nanosheets having O-terminated {100} facets.

2. The method of claim 1, further comprising
 (d) heating the anatase $TiO_2$ nanosheets having O-terminated {100} facets at a temperature ranging from about 400° C. to about 600° C. to obtain anatase $TiO_2$ nanosheets having activated {100} facets.

3. The method of claim 1, further comprising, after step (c), washing with ethanol, centrifuging and drying the anatase $TiO_2$ nanosheets having O-terminated {100} facets at a temperature ranging from room temperature to about 200° C.

4. The method of claim 1, wherein the titanium complex is a titanium (IV) complex.

5. A method of fabricating a dye-sensitized solar cell, the method comprising:
 (a) mixing a titanium complex with an ethanolamine derivative;
 (b) adding sufficient water to completely hydrolyze the titanium complex to form a mixture, the mixture comprising $Ti(OH)_4$;
 (c) heating the mixture at only one temperature ranging from about 150° C. to about 200° C. to obtain anatase $TiO_2$ nanosheets having O-terminated {100} facets;
 (d) heating the anatase $TiO_2$ nanosheets having O-terminated {100} facets at a temperature ranging from about 400° C. to about 600° C. to obtain anatase $TiO_2$ nanosheets having activated {100} facets; and
 (e) soaking the anatase $TiO_2$ nanosheets having activated {100} facets in a N719 industry standard dye solution to obtain anatase $TiO_2$ nanosheets having O-(dye)-terminated {100} facets.

6. The method of claim 5, further comprising, immediately after step (c) and before step (d), washing with ethanol, centrifuging and drying the anatase $TiO_2$ nanosheets having O-terminated {100} facets at a temperature ranging from room temperature to about 200° C.

7. The method of claim 5, wherein the titanium complex is a titanium (IV) complex.

\* \* \* \* \*